United States Patent [19]

Anik

[11] Patent Number: 4,476,116

[45] Date of Patent: Oct. 9, 1984

[54] POLYPEPTIDES/CHELATING AGENT NASAL COMPOSITIONS HAVING ENHANCED PEPTIDE ABSORPTION

[75] Inventor: Shabbir T. Anik, Palo Alto, Calif.

[73] Assignee: Syntex (U.S.A.) Inc., Palo Alto, Calif.

[21] Appl. No.: 448,547

[22] Filed: Dec. 10, 1982

[51] Int. Cl.³ .................... C07C 103/52; A61K 37/02
[52] U.S. Cl. .............................. 424/177; 260/112.5 R
[58] Field of Search .................. 260/112.5 R; 424/177

[56] References Cited

U.S. PATENT DOCUMENTS 3,803,309 4/1974 Desaulles ...................... 260/112.5 R
4,159,980 7/1979 Immer et al. ................. 260/112.5 R

FOREIGN PATENT DOCUMENTS 1454105 10/1976 United Kingdom .
2092002 8/1982 United Kingdom .

Primary Examiner—Delbert R. Phillips
Assistant Examiner—F. Moezie
Attorney, Agent, or Firm—James M. Kanagy; Tom M. Moran

[57] ABSTRACT

Disclosed herein are nasal spray compositions and methods for enhancing polypeptide absorption across nasal membranes comprising a chelating agent and a polypeptide in a pharmaceutically acceptable excipient.

14 Claims, No Drawings

POLYPEPTIDES/CHELATING AGENT NASAL COMPOSITIONS HAVING ENHANCED PEPTIDE ABSORPTION

BACKGROUND OF THE INVENTION

The present invention relates to novel polypeptide formulations which demonstrate enhanced absorption across nasal membranes. More particularly, the present invention relates to polypeptide-containing pharmaceutical formulations having chelating agents which enhances peptide absorption across nasal mucous membranes.

PRIOR ART

Pharmaceutically active polypeptides are usually administered solely by injection. Other methods of administration, for example, oral administration, intratrachial administration and rectal administration, have been investigated but the results seldom if ever are satisfactorily comparable to that of injection. While it is more desirable and more elegant to be able to administer drugs orally or across mucous membranes or the skin, these routes of administration have heretofor required the administration of much higher amounts of active ingredient relative to administration by injection.

Oral administration usually results in gastric or enzymatic hydrolysis of a substantial amount of the protein into subunits which do not retain the biological activity of the parent compound. Attempts to administer polypeptides across membrane barriers, such as mucous membranes or the skin, have not met with great success for a number of reasons, incuding retention of the peptide by the skin or membrane as well as degradation during the absorption process.

Several references relating to the enhancement of peptide absorption across mucous membranes are listed herewith. British patent application No. 2,092,002 discloses vaginal and rectal suppository and injectable polypeptide formulations containing a chelating agent absorption promoter with the presence of salt, e.g. NaCl, at concentrations higher than required to achieve an isotonic solution. Feldman, S. and Gibaldi, M., *J. Pharm. Sci.*, Vol. 58, 968–970 (1969) report a small but statistically significant increase in the intestinal transfer rate of salicylate across everted rat intestine after the intestine had been exposed to 25 mM EDTA but which chelating agent had no significant effect on salicylamide transfer. Cascella, P. J. et al, have reported in *J. Pharm. Sci.*, Vol. 70, 1128–1131 (1981) that the time to produce death in goldfish exposed to secobarbatial sodium could be altered by first exposing goldfish to disodium EDTA in their tanks. Cornheim, G. E., *Nature*, 190, 236 (1961) relate that the sodium salt of EDTA was capable of enhancing the absorption of heparin in synthetic heparinoids from the GI tract of rats and dogs. This work was later confirmed in other animals by M. A. Seidell in *Clin. Res.*, 8, 246 (1960).

It has now been found that chelating agents substantially enhance polypeptide absorption across nasal membranes. This increased absorption is sufficiently great that it is now feasible to design nasal formulations for administration of polypeptide.

SUMMARY OF THE INVENTION

This invention relates to a nasal spray composition having enhanced polypeptide absorption which composition comprises 0.00005 to 10% weight/weight (w/w) of a pharmaceutically active polypeptide; 0.05 to 10% w/w of a pharmaceutically acceptable chelating agent; and a pharmaceutically acceptable excipient in a quantity sufficient to make weight.

The invention also relates to a method for enhancing the absorption of pharmaceutically active polypeptides across a nasal membrane which method comprises adding 0.05 to 10% weight/weight (w/w) of a pharmaceutically acceptable chelating agent to a nasal spray composition comprising polypeptide drugs in an amount of 0.00005 to 10% w/w and a suitable nasal spray forming excipient in a quantity sufficient to make weight.

DETAILED DESCRIPTION OF THE INVENTION

The present invention relates to a novel pharmaceutical formulation suitable for application to nasal membranes which comprises a polypeptide, an absorption enhancing chelating agent and one or more excipients as are necessary to prepare a working nasal spray composition.

The active ingredients of this invention are peptide materials herein referred to as polypeptides and which exert some pharmaceutical activity on the body in the sense that they would be viewed as a drug as opposed to nutritional or energy producing peptides.

The word "polypeptide" as used herein refers to a peptide which upon hydrolysis yields more than two amino acids; called tripeptides, tetrapeptides, etc. according to the number of amino acids contained in the chain. In addition such compounds will have drug activity in that the compound may be used on or administered to humans or animals as an aid in the diagnosis, treatment, or prevention of disease or other abnormal condition, for the relief of pain or suffering, or to control or improve any physiological or pathological condition.

Polypeptides may be readily classified by biological function such as, for example, enzymes, storage proteins, transport proteins, contractile proteins, protective proteins, toxins, hormones, and structural proteins. While any or all of the proteins exemplified by these several classifications may exhibit drug-like activity, those of particular interest for this invention are the enzymes, protective proteins and hormones. Of greatest interest are the protective proteins and hormones.

Enzymatic proteins of interest herein may be, for example, nucleases, cytochromes and protein degrading enzymes. Protective polypeptides are exemplified by antibody proteins, fibrinogin, and thrombin along with those proteins having antiviral activity such as interferon and its various subunits.

The polypeptides of greatest interest herein are those proteins generally characterized as having hormonal activity. These materials most frequently are employed as replacement therapy because the body does not produce the proper amount or is producing an inactive or less active polypeptide.

Examples of such hormonal polypeptides are insulin, adrenocorticotrophic hormone usually abbreviated ACTH and, of developing importance, growth hormone and related peptides. Another group of hormones and hormonal analogs being developed are those related to fertility control. More specifically human chorionic gonatatropin, follicule stimulating hormone, luteinizing hormone and luteinizing hormone releasing hormone agonists and antagonists have been made and are in various developmental stages for the treatment of physiological conditions normally effected or controlled by the activity of such hormones related to fertility.

Other proteins of interest are globulin proteins involved with the body's immune response mechanism. For example thymosin and thymosin analogs protentiate the autoimmune response; and thyroid stimulating polypeptides fall into this classification.

One preferred polypeptide family herein is that of interferon. Interferon is really a group of proteins produced in infected eukaryotic cells which have antiviral activity. Human interferon (IFN) is presently known to exist in at least three forms, alpha, beta and gamma and to arise from at least two sources, human fibroblasts and leukocytes. IFN-alpha has a molecular weight between 18,500–22,000. IFN-$\beta$ has been assigned a molecular weight of between 22,000–26,000. The gamma form is presently being investigated having several molecular weight ranges assigned, e.g. 65,000–70,000 by one investigator and 40,000–46,000 by another. Attempts to resolve or explain these differences in IFN-gamma are ongoing.

Production of all IFN materials is presently difficult due to the very small amounts produced by standard cell fermentation methods. This fact is directly responsible for the lack of precise IFN characterization experienced by IFN research to date. With the cloning of the human fibroblast IFN gene by Taniguchi et al, *Gene* 1980 and the human leukocyte IFN gene by Nagata et al, *Nature* 1980, genetic engineering techniques may provide more substantial quantities for therapeutic use. Present fermentation production methodologies are discussed and described in *Interferon: A Primer* by Freidman, R. M., pp. 26–45, Academic Press 1981 and *Interferon 2*, Knight, E. Jr., pp. 1–11 Academic Press, Gresser, I. Ed (1980).

A second polypeptide of particular interest herein is insulin, including both animal and human insulin in its various forms and from its several sources. Insulin from one species may be used in the treatment of diabetes in other species so that any or all insulins are within the scope of this invention.

The structure of insulin is well-known, having first been determined by Sanger and Tuppy, *Biochem. J.* 49, 463, 481 (1951). Insulin may be synthetically prepared or, as is most frequently done, derived from the pancreas of slaughtered animals, Genetic engineering techniques have now been advanced to the state where human insulin can be produced in economically viable quantities by bacteria. Production of human insulin by recominant DNA techniques may be found in European patent application No. 55945. Approaches to commercial synthesis of insulin have been summarized in *Chem. and Engineering News*, 52, 19 (1974).

A number of insulin preparations are commercially available but all fall into two categories. One category is pure insulin from a beef or pork source. The other is insulin from these two sources which additionally contains zinc in some varying amount.

Another preferred polypeptide herein is human growth hormone (hGH), a polypeptide which plays a central role in bone development, and in connective tissue and skeletal muscle development. Human growth hormone is a 191 residue polypeptide with a molecular weight of 22,128. It has been accorded an amino acid sequence as follows:

HUMAN GROWTH HORMONE

|     | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|-----|---|---|---|---|---|---|---|---|---|----|----|----|----|----|----|----|----|----|----|----|----|----|----|----|----|----|----|----|----|----|
| 1   | F | P | T | I | P | L | S | R | L | F  | D  | N  | A  | M  | L  | R  | A  | H  | R  | L  | H  | Q  | L  | A  | F  | D  | T  | Y  | Q  | E  |
| 31  | F | E | E | A | Y | I | P | K | E | Q  | K  | Y  | S  | F  | L  | Q  | N  | P  | Q  | T  | S  | L  | C  | F  | S  | E  | S  | I  | P  | T  |
| 61  | P | S | N | R | E | E | T | Q | Q | K  | S  | N  | L  | Q  | L  | L  | R  | I  | S  | L  | L  | L  | I  | Q  | S  | W  | L  | E  | P  | V  |
| 91  | Q | F | L | R | S | V | F | A | N | S  | L  | V  | Y  | G  | A  | S  | N  | S  | D  | V  | Y  | D  | L  | L  | K  | D  | L  | E  | E  | G  |
| 121 | I | Q | T | L | M | G | R | L | E | D  | G  | S  | P  | R  | T  | G  | Q  | I  | F  | K  | Q  | T  | Y  | S  | K  | F  | D  | T  | N  | S  |
| 151 | H | N | D | D | A | L | L | K | N | Y  | G  | L  | L  | Y  | C  | F  | R  | K  | D  | M  | D  | K  | V  | E  | T  | F  | L  | R  | I  | V  |
| 181 | Q | C | R | S | V | E | G | S | C | G  | F  |    |    |    |    |    |    |    |    |    |    |    |    |    |    |    |    |    |    |    |

COMPOSITION

| | | | |
|---|---|---|---|
| 7 ALA A | 14 GLN Q | 26 LEU L | 18 SER S |
| 11 ARG R | 13 GLU E | 9 LYS K | 10 THR T |
| 9 ASN N | 8 GLY G | 3 MET M | 1 TRP W |
| 11 ASP D | 3 HIS H | 13 PHE F | 8 TYR Y |
| 4 CYS C | 8 ILE I | 8 PRO P | 7 VAL V |

Two disulfide bridges are present in this molecule, one linking residues 67 and 165 and a second linking residues 182 and 189. This amino acid sequence of human growth hormone is set out in the *Atlas of Protein Sequence and Structure*, Vol. 5, Suppl. 3, P. S-5, Dehoff, M. O., et al, National Biomedical Research Foundation, Washington, D.C. (1973).

A subsequent publication by J. A. Martial, et al, in *Science*, 205:602–607 (1979), sets out the complementary DNA neuclotide sequence for hGH. The DNA sequence predicts glutamine, asparagine, glutamine, glutamic acid, glutamine, aspartic acid, asparagine, and glutamine at positions 29, 47, 49, 74, 91, 107, 109 and 122 respectively while the Atlas of Protein Sequence and Structure sequence obtained by degradative protein sequencing indicates glutamic acid, aspartic acid, glutamic acid, glutamine, glutamic acid, asparagine, aspartic acid, and glutamic acid at these respective positions.

Availability of hGH has until recently been limited to that which could be extracted from the pituitary gland of human cadavers. However, recombinant DNA techniques have made it possible recently to produce from bacteria biologically active hGH in relatively substantial quantities. See, for example, J. A. Martial, et al, *Science*, 205:602–607 (1979).

Another preferred polypeptide, a peptide related to human growth hormone, is a 44 amino acid peptide identified as growth hormone-releasing factor and which has been isolated and sequenced by R. Guillemin, et al, *Science*, Vol. 218, 585–587 (1982). The amino acid sequence and its present source are described in the foregoing reference and is as follows:

H-Tyr-Ala-Asp-Ala-Lle-Phe-Thr-Asn-Ser-Tyr-Arg-
   Lys-Val-Leu-Gly-Gln-Leu-Ser-Ala-Arg-Lys-Leu-
   Leu-Gln-Asp-Lle-Met-Ser-Arg-Gln-Gln-Gly-Glu-

Ser-Asn-Gln-Glu-Arg-Gly-Ala-Arg-Ala-Arg-Leu-NH₂.

Human growth hormone-releasing factor is presently available only from human pancreatic islet cell tumors and variously located carcinoids. A fuller discussion is available in the Guillemin reference supra.

Peptides having thymic activity also constitute a preferred embodiment of this invention. Thymic peptides of greatest interest in this invention are represented by the following formula.

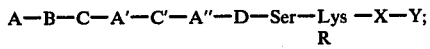

wherein:
A, A' and A" are each independently Gly, D-Ala, D-Leu, or D-Trp; wherein A may optionally be N-alkylated or N-acylated;
B is Pro, Δ³-Pro, Thz, or diMeThz;
C and C' are each independently Thr, Ser, Val, or alloThr;
D is Glu, Gln, Asp, or Asn;
R is hydrogen or lower alkyl or lower acyl, substituted for one of the hydrogens on the ε-amino group of the lysyl residue;
X is Cys; Ala, ABU, or Cys(Me); and
Y is selected from the group consisting of hydroxy, Pro, Pro-Leu, and Pro-Leu-Met, —NH₂, ProNH₂, Pro-LeuNH₂ and Pro-leu-MetNH₂; and to the pharmaceutically acceptable salts thereof. Specifically, these peptides are decapeptides of the formula:

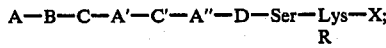

undecapeptides of the formula,

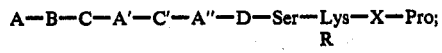

dodecapeptides of the formula,

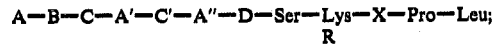

and tridecapeptides of the formula,

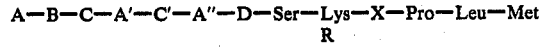

wherein A, A', A"; B; C and C'; D; R; and X are as defined above.

These synthetic peptides demonstrate thymic activity. They are fully discussed and set out in U.S. Pat. No. 4,320,118, issued in March of 1982. A full description of the nomenclature, synthetic preparative methods, test procedures, a general and specific disclosure of the various synthetic peptides covered, a recitation of pharmaceutically acceptable salts for these peptides and various other materials necessary for a full and complete understanding of the scope of these peptides may be found there. That patent is incorporated in full herein by reference and made a part hereof.

Especially preferred thymic peptide analogs are those embodiments wherein A, A' and A" are each independently Gly or D-ala and wherein A may optionally be alkylated or acylated at the α-amino group; D is Glu or Gln and X is Ala or Cys.

Another preferred set of embodiments is that wherein Y is —OH, —NH₂, Pro, or ProNH₂.

In a further instance a preferred group of polypeptides are the analogs of LHRH. Agonist and antagonist analogs of LHRH have been prepared and found to be useful in the control of fertility in both male and female; and useful in the reduction in accessory organ weight in male and female; will promote weight gain in domestic animals is feedlot situations; will stimulate abortion in pregnant animals; and in general act as chemical sterilants.

The natural luteinizing hormone releasing hormone, LHRH, is a decapeptide comprised of naturally occurring amino acids (which have the L-configuration except for the achiral amino acid glycine). Its sequence is as follows:

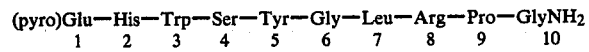

A large number of analogs of this natural material have been prepared and studied in attempts to find compounds which have greater agonist activity or exhibit antagonist activity.

By far the most significant modification for the enhancement of agonist activity is obtained by changing the 6-position residue from Gly to a D-amino acid. In addition, substantial increased agonist activity is obtained by eliminating the Gly—NH₂ in position 10 to afford a nonapeptide as an alkyl, cycloalkyl or fluoroalkylamide or by replacing the Gly—NH₂ by an α-azaglycine amide. In yet other instances modifications have been made at positions 1 and 2 in attempts to enhance agonist activity.

In addition to the preparation of agonist analogs, a number of nona- and decapeptides have been prepared which are competitive antagonists to LHRH; all of which require deletion or replacement of the histidine residue at position 2. In general, it appears that a D-amino acid placed in the sequence at that position gives the best antagonist activity. It has also been shown that adding a modification at the 6 position, which, without the modification at position 2 results in the agonist activity noted above, enhances the antagonist activity of the 2-modified analogs. Additional increments in antagonist activity may be had by modifying positions 1, 3 and/or 10 in the already 2, 6 modified peptide. It has also been shown that N-acylation of the amino acid at position 1 is helpful.

This invention has application to LHRH and all synthetic agonist and antagonist analogs thereof. The patent and periodical literature is replete with nona- and decapeptides of this type. It is intended that all such compounds will be within the scope of this invention.

Nona- or decapeptides having LHRH agonist or antagonist activity are disclosed, along with processes for preparation thereof, in the following U.S. Pat. Nos. 3,813,382; 3,842,065; 3,849,389; 3,855,199; 3,886,135; 3,890,437; 3,892,723; 3,896,104; 3,901,872; 3,914,412; 3,915,947; 3,929,759; 3,937,695; 3,953,416; 3,974,135;

4,010,125; 4,018,914; 4,022,759; 4,022,760; 4,022,761; 4,024,248; 4,034,082; 4,072,668; 4,075,189; 4,075,192; 4,086,219; 4,101,538; 4,124,577; 4,124,578; 4,143,133; 4,234,571; 4,253,997; 4,292,313; 4,341,767.

LHRH analogs disclosed in these patents are incorporated herein by reference as if set out in full herein. This list is not intended to be exhaustive of all U.S. Patents covering LHRH analogs but does represent the majority; nor is this invention limited exclusively to the compounds disclosed in the recited patents.

Of the numerous LHRH analogs disclosed by the foregoing patents and in the periodical literature, there are certain compounds which have been shown to be preferred for the control of fertility, enhancement of growth, treatment of prostatic cancer, for inducing abortion and other situations where LHRH agonists or antagonists have utility.

One such group of agonist compounds if LHRH analogs disclosed in U.S. Pat. No. 4,234,571 represented by the following formula:

(pyro)Glu-His-V-Ser-W-X-Y-Arg-Pro-Z       (I)

and the pharmaceutically acceptable salts thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue

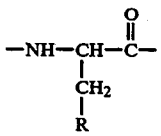

wherein
R is
   (a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or
   (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoleucyl, nor-leucyl or N-methyl-leucyl;

Z is glycinamide or —NR—R$^1$, wherein R$^1$ is lower alkyl, cycloalkyl, fluoro lower alkyl or

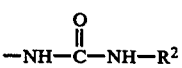

wherein
R$^2$ is hydrogen or lower alkyl.

More preferred are those compounds of Formula I wherein V is tryptophyl or phenylalanyl; W is tyrosyl; X is 3-(2-naphthyl)-D-alanyl or 3-(2,4,6-trimethylphenyl)-D-alanyl; Y is leucyl or N-methyl-leucyl; and Z is glycinamide or —NHEt.

Particularly preferred compounds of Formula I are:
(pyro) Glu-His-Trp-Ser-Tyr-3-(2-naphthyl)-D-alanyl-Leu-Arg-Pro-Gly-NH$_2$;
(pyro) Glu-His-Trp-Ser-Tyr-3-(2-naphthyl)-D-alanyl-N-methyl-Leu-Arg-Pro-Gly-NH$_2$;
(pyro)Glu-His-Phe-Ser-Tyr-3-(2-naphthyl)-D-alanyl-Leu-Arg-Pro-Gly-NH$_2$;
(pyro) Glu-His-Trp-Ser-Tyr-3-(2,4,6-trimethylphenyl)-D-alanyl-Leu-Arg-Pro-Gly-NH$_2$,
(pyro) Glu-His-Trp-Ser-Tyr-3-(2-(naphthyl)-D-alanyl-Leu-Arg-Pro-NHEt, and
(pyro) Glu-His-Trp-Ser-Tyr-3-(2-naphthyl)-D-alanyl-N-methyl-Leu-Arg-Pro-NHEt, and their pharmaceutically acceptable salts.

Further particularly preferred agonist compounds from other U.S. Patents and the periodical literature are:
(pyro) Glu-His-Trp-Ser-Tyr-D-Trp-Leu-Arg-Pro-GlyNH$_2$, Coy, C. D., *J. Med. Chem.*, 19, 423(1976);
(pyro) Glu-His-Trp-Ser-Tyr-D-Trp-N-Me-Leu-Arg-Pro-NHEt, Conbin, A. & Bex, F. J., "LHRH Peptides as Femal e and Male Contraceptives," Shelton, J. D. & Sciarra, J. J., Ed., Harper & Row, Philadelphia (1981), pp 68–84;
(pyro) Glu-His-Trp-Ser-Tyr-D-Trp-Leu-Arg-Pro-NHEt; Rivier, J. et al, "Peptides: Chemistry, Structure and Biology—Proceedings of the Fourth American Peptide Symposium," R. Walter & J. Meienhofer, Eds, (1975) Ann Arbor Science Publications, p 863–870;
(pyro) Glu-His-Trp-Ser-Tyr-D-Ala-Leu-Arg-Pro-GlyNH$_2$, U.S. Pat. No. 3,914,412;
(pyro) Glu-His-Trp-Ser-Tyr-D-Leu-Leu-Arg-Pro-NHEt; Fujino, M. et al, *Biochem. Biophys. Res. Commun.*, 60, 406 (1974;
(pyro) Glu-His-Trp-Ser-Tyr-D-Leu-Leu-Arg-Pro-GlyNH$_2$, U.S. Pat. No. 3,914,412;
(pyro) Glu-His-Trp-Ser-Tyr-D-Ser(t-But)-Leu-Arg-Pro-NHEt, U.S. Pat. No. 4,024,248;
(pyro) Glu-His-Trp-Ser-Tyr-D-Ser(t-But)-Leu-Arg-Pro-NHEt, Konig, W., et al, "Peptides: Chemistry, Structure and Biology—Prodeedings of the Fourth American Peptide Symposium," R. Walter & J. Meienhofer, Eds, (1975), Ann Arbor Science Publications, p 883–888;
(pyro) Glu-His-Trp-Ser-Tyr-D-Ser(t-But)-Leu-Arg-AzaGly, Dutta, A. S., et al, *Biochem. Biophys. Res. Commum.* 81, 382 (1978);
(pyro) Glu-His-Trp-Ser-Tyr-D-His(Bzl)-Leu-Arg-Pro-NHEt, Vall, W. et al, "Peptides: Studies and Biological Function—Proceedings's of the Sixth American Peptide Symposium," E. Gross & J. Meienhofer, Eds, Pierce Chem Co. (1979) pp 781–793;
(pyro) Glu-His-Trp-Ser-Tyr-D-pentamethyl-Phe-Leu-Arg-Pro-GlyNH$_2$, Coy, D. H., "Clinical Neurological Endocrinology—A Pathological Physical Approach," G. Tol Ed, (1979) p 83; and
(Pyro) Glu-His-Trp-Ser-Tyr-3-(2-naphthyl)-D-alanyl-Leu-Arg-Pro-GlyNH$_2$, Nestor, J. Jr et al, *J. Med. Chem.*, 25, 795 (1982).

Preferred antagonist analogs of LHRH are the nona- and decapeptides disclosed in U.S. Pat. No. 4,341,767 and U.S. Application Ser. No. 387,101 filed June 10, 1982 represented by Formula (II):

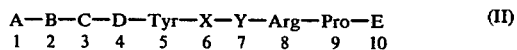

and the pharmaceutically acceptable salts thereof, wherein:

X is N,N'-guanido-disubstituted-D-argininyl or D-homoargininyl, D-argininyl, D-lysyl, or D-alanyl residue wherein one hydrogen on C-3 of the D-alanyl is replaced by:
(a) a carbocyclic aryl-containing radical selected from the group consisting of phenyl substituted with three or more straight chain lower alkyl or alkoxy groups, trifluoromethyl, naphthyl, anthryl, fluorenyl, phenanthryl, biphenylyl and benzhydryl; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl, and adamantyl; or
(c) a heterocyclic aryl containing radical selected from the group consisting of radicals represented by the following structural formulas:

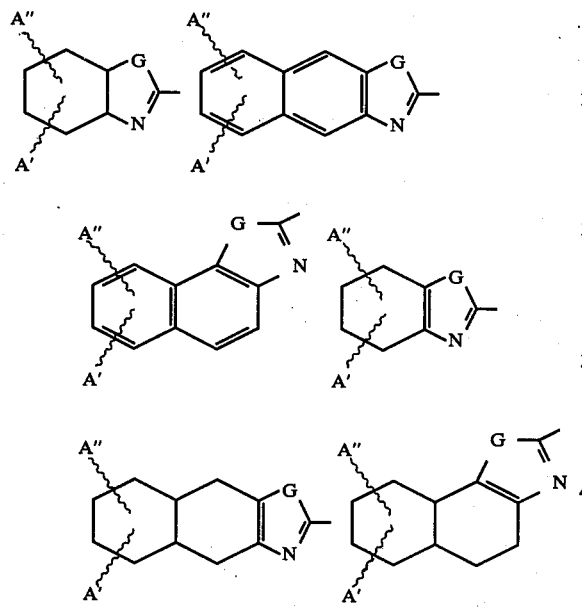

wherein
A″ and A′ are independently selected from the group consisting of hydrogen, lower alkyl, chlorine, and bromine, and G is selected from the group consisting of oxygen, nitrogen, and sulfur;
A is an amino acyl residue selected from the group consisting of L-pyroglutamyl, D-pyroglutamyl, N-acyl-L-prolyl, N-acyl-D-prolyl, N-acyl-D-tryptophanyl,
N-acyl-D-phenylalanyl, N-acyl-D-p-halophenylalanyl,
N-acyl-D,L-seryl, N-acyl-D,L-threonyl, N-acyl-glycyl,
N-acyl-D,L-alanyl, N-acyl-L-alkylprolyl, and N-acyl-X
wherein
X is as defined previously;
B is an amino acyl residue selected from the group consisting of D-phenylalanyl, D-p-halophenylalanyl, 2,2-diphenylglycyl, and X wherein X is as defined previously;
C is an amino acyl residue selected from the group consisting of L-tryptophanyl, D-tryptophanyl, D-phenylalanyl, D-phenylalanyl and X wherein X is as defined above;
D is an amino acyl residue selected from the group consisting of L-seryl, and D-alanyl;
Y is an amino acyl residue selected from the group consisting of L-leucyl, L-norleucyl and L-norvalyl;
E is D-alanyl, glycinamide or —NH—R¹, wherein R¹ is lower alkyl, cycloalkyl, fluoro lower alkyl or —NH—CO—NH—R² wherein R² is hydrogen or lower alkyl; are disclosed.

The most preferred embodiments of Formula II are:
N-Ac-Pro-D-p-F-Phe-D-Nal(2)-Ser-Tyr-D-Nal(2)-Leu-Arg-Pro-GlyNH₂;
N-Ac-Pro-D-p-Cl-Phe-D-Nal(2)-Ser-Tyr-D-Nal(2)-Leu-Arg-Pro-GlyNH₂;

Also especially preferred are the following compounds which are disclosed in the noted patent and periodical literature:
N-Ac-Δ³ Pro-D-p-F-Phe-D-Nal(2)-Ser-Tyr-D-Nal(2)-Leu-Arg-Pro-GlyNH₂, Rivier, J., et al, "LHRH Peptides as Female and Male Contraceptives," G. I. Zatuchni, J. D. Shelton & J. J. Sciarra, Eds, Haper & Row, Philadelphia (1981), pp 13–23;
N-Ac-Δ³Pro-D-p-Cl-Phe-D-Trp-Ser-Tyr-D-Trp-N-Me-Leu-Arg-Pro-GlyNH₂, Rivier, J., et al, Science, 210, 93 (1980);
N-Ac-D-p-Cl-Phe-D-p-Cl-Phe-D-Trp-Ser-Tyr-D-Trp-Leu-Arg-Pro-AlaNH₂, Erchigyi, Peptides, 2, 251 (1981);
N-Ac-D-p-Cl-Phe-D-p-Cl-Phe-D-Trp-Ser-Tyr-D-Arg-Leu-Arg-Pro-D-AlaNH₂, Coy, D. H., Endocrinology, 110, 1445 (1982); and
N-Ac-D-Nal(2)-D-p-F-Phe-D-Trp-Ser-Tyr-D-Arg-Leu-Arg-Pro-GlyNH₂, Rivier, J., et al, Contraceptive Delivery Systems, 3, 67 (1982).

The amount of polypeptide present in these formulations will be between 0.00005 percent to 10 percent by weight/weight (w/w). More preferably the active ingredient will be present in an amount of 0.0005 to 5 percent w/w but most preferably the active ingredient of these compositions will be present in an amount of 0.01 percent w/w.

Enhanced polypeptide absorption across a nasal membrane is effected by the presence of a pharmaceutically acceptable chelating agent. As used herein the term "pharmaceutically acceptable" refers to the fact that said chelating agents will not have an untoward or deleterious effect on the host to which they are being administered or cause unacceptable mucosal membrane irritation and/or toxicity when used in the normal and usual course of drug administration.

There may be employed a chelating agent which has a functional group capable of forming a ring containing a metal ion. More preferably, the chelating agent will be one containing at least one functional group having a proton capable of being displaced by said metal ion or an exchangeable metal ion (e.g. hydroxyl group, carboxyl group, imino group, etc.); or a group capable of coordination bonding to the metal ion (e.g. carbonyl group, amino group etc.). Typical examples of such compounds are enumerated below, but the present invention is not limited thereto.

Oxalic acid, malonic acid, succinic acid, maleic acid, fumaric acid, aconitic acid, pimelic acid, sebacic acid, allymalonic acid, ethylmalonic acid;

Citric acid, malic acid, glyceric acid, tartaric acid, mevaloic acid, oxyglutaric acid;

Oxaloacetic acid, α-ketoglutaric acid, β-ketoglutaric acid, α-ketomalonic acid, glucuronic acid, galacturonic acid, mannuronic acid; aspartic acid, glutamic acid, glycine, alanine, lysine, hystidine, alginine, cysteine, ε-aminocaproic acid, phenylalanine, phenylglycine, p-hydroxyphenylglycine, p-aminophenylalanine, γ-carboxyglutamic acid;

Iminodiacetic acid, hydroxyethyliminodiacetic acid, ethylenediaminediacetic acid, ethylenediaminetetraacetic acid, trans-cyclohexanediaminetetraacetic acid, diethylenediaminepentaacetic acid, β-alaninediacetic acid, diaminopimelic acid;

Phthalic acid, terephthalic acid, homophthalic acid, phenylsuccinic acid, phenylmalonic acid, oxanylic acid-o-carboxylic acid, anthralininoacetic acid, 2,4-dihydroxybenzoic acid, p-aminosalicyclic acid, phthalyglutamic acid, kynurenine;

1,2-hyroxybenzene-3,5-disulfonic acid, 4-aminophenol-2-sulfonic acid, cysteic acid; 2-phosphoglyceric acid, glycero-3-phosphoric acid, glucose-1,6-diphosphoric acid, fructose-1,6-diphosphoric acid.

Chelating agents are employed in these formulations either as the parent molecule or in the salt form where appropriate. For example, compounds containing an acid function may be used in the protonated form or as a pharmaceutically acceptable inorganic or organic salt which retains the chelating activity of the parent compound.

The pharmaceutically acceptable salts will be any salt which retains the phenomena of enhanced peptide absorption and which is not deleterious to the subject or otherwise contraindicated. Such salts are for example those salts derived from inorganic bases which include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

Preferably the chelating agent will be a multifunctional acidic compound in the salt form, preferably an alkali metal salt. Alkali metal salt refers to the sodium, potassium, magnesium or calcium salts of any subject chelating agent having at least one acid group. Where the chelating agent has more than one acid function one or more of the acid functions may be in the salt form. For example, EDTA may be used as the mono, di, tri or tetrasodium salt or the disodium, monocalcium salt may be used as an alternative. The most preferred chelating agent herein are the alkali metal salts of EDTA. Most preferred are the mono and disodium salt of EDTA.

The amount of chelating agent used in the practice of this invention will be that amount which increases the absorption of polypeptides over that of a similar composition which does not contain the chelating agent. That amount will be somewhere between 0.005 to 10 percent weight/weight (w/w) of the final formulation. Preferably, the chelating agent will be present in an amount between 0.05 to 5 percent, most preferably some amount between 0.1 to 5 percent w/w.

The pharmaceutically active polypeptides and chelating agents will be confected with one or more pharmaceutically acceptable excipients which result in a composition suitable for administering the polypeptide across the nasal membranes as a spray or aerosol.

The subject nasal formulations may be formulated in water or an acceptable aerosol composition. Preferably they will be formulated as a nasal spray solution with water or in buffer at a pH of between about 3.0 and 8.0, most preferably pH 5.0–5.4, by means of some pharmaceutically acceptable buffer system. Any pharmaceutically acceptable buffering system capable of maintaining a pH in the denoted range may be used for the practice of this invention. A typical buffer will be, for example, an acetate buffer, a phosphate buffer, a citrate buffer, a succinate buffer or the like. The buffer of choice herein is an acetate buffer in a concentration of between 0.005 and 0.1 molar, most preferably 0.02 molar. Water or buffer solution is added to the active ingredient and the chelating agent in a quantity sufficient to make volume.

Other materials such as preservatives, surfactants, co-solvents, antioxidants, salts or other materials to impart the tonic value to the solutions, or other additives indicated by known nasal formulation chemistry may be added to these formulations.

Aerosol formulations are prepared as per known techniques and composition profiles.

The invention is illustrated by the following nonlimiting examples.

EXAMPLE 1

6.25 milligrams of (pyro)Glu-His-Trp-Ser-Tyr-3-(2-naphthyl)-D-alanyl-Leu-Arg-Pro-Gly-NH$_2$ were dissolved in 5 ml of a 0.02 molar acetate buffer solution having a pH of about 5.2 in a volumetric flask. A hundred milligrams of disodium EDTA were then dissolved in this solution which is brought almost to volume, the pH adjusted to 5.2 plus or minus 0.2 and then a volume of buffer added in a quantity sufficient to make 10 ml.

EXAMPLE 2

12.5 mg of (pyro)Glu-His-Trp-Ser-Tyr-3-(2-naphthyl)-D-Ala-Leu-Arg-Pro-Gly-NH$_2$ were dissolved in 3 ml of 0.02M acetate buffer along with 0.5 g of sorbitol, 0.001 g of benzalkonium chloride and 0.01 g of disodium EDTA. This mixture was thoroughly agitated to insure complete solvation of all components and then brought to volume (10 ml) with acetate buffer. The final solution had a pH of 5.2/±0.2.

When administered as a nasal spray to monkeys, this composition showed a peak level of 5.3 ng/ml of plasma versus 1.8 ng/ml for controls (no disodium EDTA) and an average area under the curve at 8 hours of 7.7 for the test animals versus 4.1 for controls. Test animals received an average dose of 226 μg/animal while controls received an average of 272 μg/animal.

EXAMPLE 3

6.25 milligrams of (pyro) Glu-His-Trp-Ser-Tyr-D-Trp-Leu-Arg-Pro-GlyNH$_2$, were dissolved in 5 ml of a 0.02 molar acetate buffer solution having a pH of about 5.2 in a volumetric flask. A hundred milligrams of disodium EDTA were then dissolved in this solution which is brought almost to volume, the pH adjusted to 5.2 plus or minus 0.2 and then a volume of buffer added in a quantity sufficient to make 10 ml.

EXAMPLE 4

12.5 mg of N-Ac-Pro-D-p-F-Phe-D-Nal(2)-Ser-Tyr-D-Nal(2)-Leu-Arg-Pro-GlyNH$_2$ were dissolved in 3 ml of 0.02M acetate buffer along with 0.5 g of sorbitol, 0.001 g of benzalkonium chloride and 0.01 g of disodium EDTA. This mixture was thoroughly agitated to insure complete solvation of all components and then brought to volume (10 ml) with acetate buffer. The final solution had a pH of 5.2/±0.2.

What is claimed is:

1. A nasal spray composition having enhanced polypeptide absorption which comprises 0.00005 to 10% weight/weight (w/w) of a pharmaceutically active polypeptide; 0.005 to 10% w/w of a pharmaceutically acceptable chelating agent; and a pharmaceutically acceptable excipient in a quantity sufficient to make weight.

2. The composition of claim 1 wherein said polypeptide is a nona- or decapeptide having LHRH agonist or antagonist activity.

3. The composition of claim 2 comprising 0.0005 to 5% w/w of said polypeptide; 0.05 to 5% w/w of said chelating agent; and aqueous buffered solution in a quantity to make weight.

4. The composition of claim 3 wherein said polypeptide is an LHRH agonist represented by Formula (I)

(pyro)Glu-His-V-Ser-W-X-Y-Arg-Pro-Z    (I)

and the pharmaceutically acceptable salts thereof wherein:

V is tryptophyl, phenylalanyl or 3-(1-naphthyl)-L-ala-nyl;

W is tyrosyl, phenylalanyl or 3-(1-pentafluorophenyl)-L-alanyl;

X is a D-amino acid residue

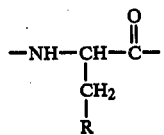

wherein

R is (a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoleucyl, nor-leucyl or N-methyl-leucyl;

Z is glycinamide or —NR—R$^1$, wherein R$^1$ is lower alkyl, cycloalkyl, fluoro lower alkyl or

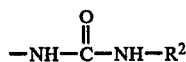

wherein

R$^2$ is hydrogen or lower alkyl and the chelating agent is an alkali metal salt of ethylenediaminetetraacetic acid (EDTA).

5. The composition of claim 4 wherein said polypeptide is present in an amount of 0.0005 to 5% w/w and said chelating agent is present in an amount of 0.05 to 5% w/w.

6. The composition of claim 5 wherein said compound is (pyro)Glu-His-Trp-Ser-Tyr-3-(2-naphthyl)-D-alanyl-Leu-Arg-Pro-Gly-NH$_2$ and its pharmaceutically acceptable salts which is present in an amount of 0.01% w/w and the chelating agent is disodium EDTA present in an amount of 0.1% w/w.

7. The composition of claim 3 wherein said polypeptide is an LHRH antagonist of Formula (II)

A—B—C—D—Tyr—X—Y—Arg—Pro—E    (II)
1   2   3   4   5    6   7   8    9    10 and the pharmaceutically acceptable salts thereof, wherein:

X is N,N'-guanido-disubstituted-D-argininyl or D-homoargininyl, D-argininyl, D-lysyl, or D-alanyl residue wherein one hydrogen on C-3 of the D-alanyl is replaced by:

(a) a carbocyclic aryl-containing radical selected from the group consisting of phenyl substituted with three or more straight chain lower alkyl or alkoxy groups, trifluoromethyl, naphthyl, anthryl, fluorenyl, phenanthryl, biphenylyl and benzhydryl; or (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl, and adamantyl; or (c) a heterocyclic aryl containing radical selected from the group consisting of radicals represented by the following structural formulas:

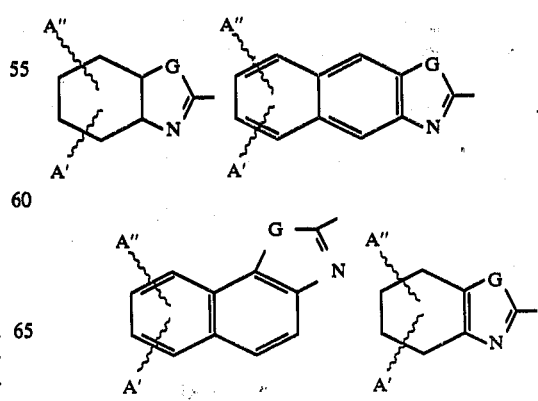

-continued

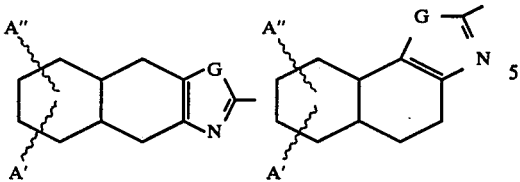

wherein
A″ and A′ are independently selected from the group consisting of hydrogen, lower alkyl, chlorine, and bromine, and G is selected from the group consisting of oxygen, nitrogen, and sulfur;

A is an amino acyl residue selected from the group consisting of L-pyroglutamyl, D-pyroglutamyl, N-acyl-L-prolyl, N-acyl-D-prolyl, N-acyl-D-tryptophanyl, N-acyl-D-phenylalanyl, N-acyl-D-p-halophenylalanyl, N-acyl-D,L-seryl, N-acyl-D,L-threonyl, N-acyl-glycyl, N-acyl-D,L-alanyl, N-acyl-L-alkylprolyl, and N-acyl-X
wherein
X is as defined previously;

B is an amino acyl residue selected from the group consisting of D-phenylalanyl, D-p-halophenylalanyl, 2,2-diphenylglycyl, and X wherein X is as defined previously;

C is an amino acyl residue selected from the group consisting of L-tryptophanyl, D-tryptophanyl, D-phenylalanyl, D-phenylalanyl and X wherein X is as defined above;

D is an amino acyl residue selected from the group consisting of L-seryl, and D-alanyl;

Y is an amino acyl residue selected from the group consisting of L-leucyl, L-norleucyl and L-norvalyl;

E is D-alanyl, glycinamide or —NH—R¹, wherein R¹ is lower alkyl, cycloalkyl, fluoro lower alkyl or —NH—CO—NH—R² wherein R² is hydrogen or lower alkyl; are disclosed.

8. A method for enhancing the absorption of pharmaceutically active polypeptides across nasal membranes which method comprises adding 0.005 to 10% weight/weight (w/w) of a pharmaceutically acceptable chelating agent to a nasal spray composition comprising 0.00005 to 10% w/w of a pharmaceutically active polypeptide and a pharmaceutically acceptable excipient in a quantity sufficient to make weight.

9. The method of claim 8 wherein said polypeptide is a nona- or decapeptide having LHRH agonist or antagonist activity.

10. The method of claim 9 which is a nasal spray composition comprising 0.0005 to 5% w/w said polypeptide; 0.05 to 5% w/w of said chelating agent; and buffer solution in a quantity sufficient to make weight.

11. The method of claim 10 wherein the polypeptide is an agonist represented by Formula (I)

(pyro)Glu-His-V-Ser-W-X-Y-Arg-Pro-Z       (I)

and the pharmaceutically acceptable salts thereof wherein:

V is tryptophyl, phenylalanyl or 3-(1-naphthyl)-L-ala-nyl;
W is tyrosyl, phenylalanyl or 3-(1-pentafluorophenyl)-L-alanyl;
X is a D-amino acid residue

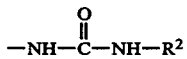

wherein
R is
(a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoleucyl, nor-leucyl or N-methyl-leucyl;
Z is glycinamide or —NR—R¹, wherein R¹ is lower alkyl, cycloalkyl, fluoro lower alkyl or

—NH—C(=O)—NH—R² wherein
R² is hydrogen or lower alkyl and the chelating agent is an alkali metal salt of ethylenidiaminetetraacetic acid (EDTA).

12. The composition of claim 11 wherein said polypeptide is present in an amount of 0.005 to 5% w/w and said chelating agent is present in an amount of 0.05 to 5% w/w.

13. The method of claim 12 wherein said polypeptide is (pyro)Glu-His-Trp-Ser-Tyr-3-(2-naphthyl)-D-alanyl-Leu-Arg-Pro-Gly-NH₂ and its pharmaceutically acceptable salts which is present in an amount of 0.01% w/w and the chelating agent is disodium EDTA present in an amount of 0.1% w/w.

14. The method of claim 9 wherein said polypeptide is an antagonist of Formula (II)

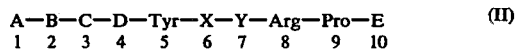

and the pharmaceutically acceptable salts thereof, wherein:

X is N,N′-guanido-disubstituted-D-argininyl or D-homoargininyl, D-argininyl, D-lysyl, or D-alanyl residue wherein one hydrogen on C-3 of the D-alanyl is replaced by:
(a) a carbocyclic aryl-containing radical selected from the group consisting of phenyl substituted with three or more straight chain lower alkyl or alkoxy groups, trifluoromethyl, naphthyl, anthryl, fluorenyl, phenanthryl, biphenylyl and benzhydryl; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl, and adamantyl; or (c) a heterocyclic aryl containing radical selected from the group consisting of radicals represented by the following structural formulas:

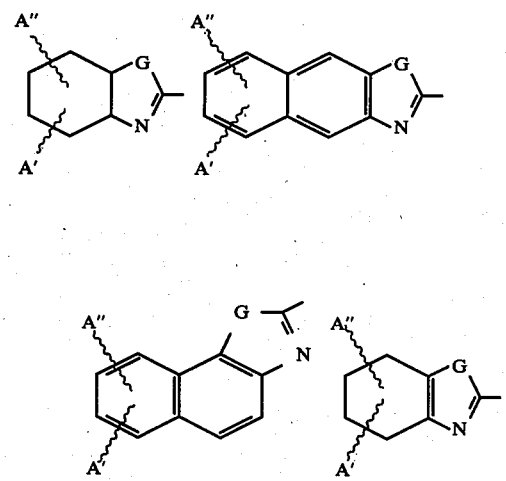

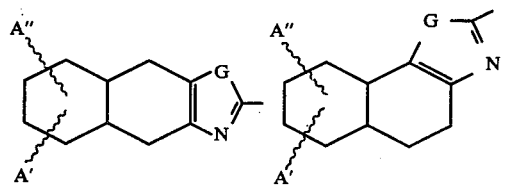

wherein
A″ and A′ are independently selected from the group consisting of hydrogen, lower alkyl, chlorine, and bromine, and G is selected from the group consisting of oxygen, nitrogen, and sulfur;

A is an amino acyl residue selected from the group consisting of L-pyroglutamyl, D-pyroglutamyl, N-acyl-L-prolyl, N-acyl-D-prolyl, N-acyl-D-tryptophanyl, N-acyl-D-phenylalanyl, N-acyl-D-p-halophenylalanyl, N-acyl-D,L-seryl, N-acyl-D,L-threonyl, N-acyl-glycyl, N-acyl-D,L-alanyl, N-acyl-L-alkylprolyl, and N-acyl-X wherein X is as defined previously;

B is an amino acyl residue selected from the group consisting of D-phenylalanyl, D-p-halophenylalanyl, 2,2-diphenylglycyl, and X wherein X is as defined previously;

C is an amino acyl residue selected from the group consisting of L-tryptophanyl, D-tryptophanyl, D-phenylalanyl, D-phenylalanyl and X wherein X is as defined above;

D is an amino acyl residue selected from the group consisting of L-seryl, and D-alanyl;

Y is an amino acyl residue selected from the group consisting of L-leucyl, L-norleucyl and L-norvalyl;

E is D-alanyl, glycinamide or —NH—$R^1$, wherein $R^1$ is lower alkyl, cycloalkyl, fluoro lower alkyl or —NH—CO—NH—$R^2$ wherein $R^2$ is hydrogen or lower alkyl.

* * * * *